United States Patent
Lee et al.

(10) Patent No.: US 11,784,553 B2
(45) Date of Patent: Oct. 10, 2023

(54) RESONANT FREQUENCY TRACKING FOR ZERO VOLTAGE SWITCHING

(71) Applicant: GOODRICH CORPORATION, Charlotte, NC (US)

(72) Inventors: Yongduk Lee, Vernon, CT (US); Matthew Robert Pearson, Hartford, CT (US); Parag M. Kshirsagar, South Windsor, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 315 days.

(21) Appl. No.: 17/336,129

(22) Filed: Jun. 1, 2021

(65) Prior Publication Data

US 2022/0385167 A1   Dec. 1, 2022

(51) Int. Cl.
*H02M 1/08* (2006.01)
*H02M 7/48* (2007.01)
(Continued)

(52) U.S. Cl.
CPC ............. *H02M 1/083* (2013.01); *A61L 2/10* (2013.01); *A61L 2/24* (2013.01); *A61L 2/26* (2013.01);
(Continued)

(58) Field of Classification Search
CPC .. H02M 1/0009; H02M 1/0058; H02M 3/156; H02M 1/083; H02M 1/4225;
(Continued)

(56) References Cited

U.S. PATENT DOCUMENTS

| 6,274,988 B1 | 8/2001 | De Vries |
| 10,418,233 B2 | 9/2019 | Larson et al. |

(Continued)

OTHER PUBLICATIONS

Suttipong Booktaklang et al: "Automatic Resonance-Frequency Tuning and Tracking Technique for a 1MHz Ultrasonic-Piezoelectric-Transducer Driving Circuit in Medical Therapeutic Applications Using dsPIC Microcontroller and PLL Techniques" International Journal of Intelligent Engineering and Systems, Mar. 31, 2019, URL: http://www.inass.org/2019/2019123102.pdf ,11 pages.

(Continued)

*Primary Examiner* — Wei (Victor) Y Chan
(74) *Attorney, Agent, or Firm* — SNELL & WILMER L.L.P.

(57) ABSTRACT

A system for controlling a power signal for zero voltage switching (ZVS) includes a voltage zero crossing detection module to detect a zero voltage condition in response to an inverter voltage from a resonant inverter crossing zero volts, and a current zero crossing detection module to detect a zero current condition in response to an inverter current from the resonant inverter crossing zero amps. The system further includes a phase detect module to detect actual phase data corresponding to an actual phase angle between the inverter voltage and the inverter current based on the zero voltage and zero current condition. The system further includes a comparator to determine a phase difference between a desired phase between the inverter voltage and the inverter current and the actual phase angle. The system further includes a controller to adjust a property of a resonant inverter to reduce the phase difference.

20 Claims, 5 Drawing Sheets

(51) Int. Cl.
| | |
|---|---|
| *A61L 2/10* | (2006.01) |
| *A61L 2/24* | (2006.01) |
| *A61L 2/26* | (2006.01) |
| *B64D 47/02* | (2006.01) |
| *H05B 41/36* | (2006.01) |
| *H01J 61/12* | (2006.01) |
| *H03L 7/085* | (2006.01) |

(52) U.S. Cl.
CPC .......... *B64D 47/02* (2013.01); *H02M 7/4815* (2021.05); *H05B 41/36* (2013.01); *A61L 2202/11* (2013.01); *A61L 2202/14* (2013.01); *A61L 2202/25* (2013.01); *H01J 61/12* (2013.01); *H03L 7/085* (2013.01)

(58) Field of Classification Search
CPC .......... H02M 1/08; H02M 1/32; H02M 3/158; H02M 3/33507; H02M 1/0032
See application file for complete search history.

(56) References Cited

U.S. PATENT DOCUMENTS

| | | | |
|---|---|---|---|
| 2010/0066260 A1* | 3/2010 | Newman, Jr. ...... | H05B 41/3921 |
| | | | 315/246 |
| 2018/0281241 A1 | 10/2018 | Schropp et al. | |

OTHER PUBLICATIONS

Kaixing Lu et al: "A Novel Efficiency-oriented Frequency Tracking Method for WPT Systems", 2019 22nd International Conference on Electrical Machines and Systems (ICEMS), IEEE, dated Aug. 11, 2019, 5 pages.

H. Karaca: "Phase detector for tuning circuit of resonant inverters" Electronics Letters, The Institution of Engineering and Technology, GB, dated May 25, 2000, 2 pages.

European Patent Office, European Search Report dated Oct. 18, 2022 in Application No. 22175670.3.

* cited by examiner

RESONANT FREQUENCY TRACKING FOR ZERO VOLTAGE SWITCHING

FIELD

The present disclosure relates to systems and methods for controlling a zero voltage switching (ZVS) power signal used to power an excimer lamp for use in aviation systems.

BACKGROUND

Ultraviolet (UV) light has been found to be an effective disinfectant. Of the various UV wavelengths, 222 nanometers (222 nm) has been found to be particularly promising (effective and relatively safe for humans in moderate doses). Currently, UV lights that emit light of this wavelength are only available as gas-discharge excimer bulbs. These bulbs require a power signal that is of relatively high voltage and relatively high frequency. Conventional power supplies for these excimer bulbs experience significant limitations, such as changing electrical properties of the excimer bulb as it is used. As a result of these changing electrical properties, the resonant frequency of the excimer bulb changes, which may result in failure of zero voltage switching used to provide the power signal. The output voltage may thus become distorted as a result. Also, relatively high current may be output at the resonant frequency point, resulting in system power loss.

Thus, there is a need in the art for systems and methods for controlling a zero voltage switching (ZVS) power signal for powering an excimer lamp.

SUMMARY

Disclosed herein is a system for controlling a power signal for zero voltage switching (ZVS). The system includes a voltage zero crossing detection module configured to detect a zero voltage condition in response to an inverter voltage from a resonant inverter crossing zero volts. The system further includes a current zero crossing detection module configured to detect a zero current condition in response to an inverter current from the resonant inverter crossing zero amps. The system further includes a phase detect module configured to detect actual phase data corresponding to an actual phase angle between the inverter voltage and the inverter current based on the zero voltage condition and the zero current condition. The system further includes a comparator configured to determine a phase difference between a desired phase between the inverter voltage and the inverter current and the actual phase angle. The system further includes a controller configured to adjust a property of a resonant inverter to reduce the phase difference based on the phase difference.

In any of the foregoing embodiments, the phase detect module includes: a voltage phase locked loop (PLL) module that receives voltage input corresponding to the zero voltage condition from the voltage zero crossing detection module; and a current PLL module that receives current input corresponding to the zero current condition from the current zero crossing detection module.

Any of the foregoing embodiments may further include an and module configured to receive an output of the voltage PLL module and an output of the current PLL module and to output an output signal in response to the output of the voltage PLL module and the output of the current PLL module both being true, wherein: the voltage PLL module further receives the output signal of the and module; the current PLL module further receives the output signal of the and module; and the actual phase data determined by the phase detect module is taken as the output of the voltage PLL module.

Any of the foregoing embodiments may further include a low pass filter configured to receive the actual phase data from the phase detect module and to output a constant value corresponding to the actual phase angle.

Any of the foregoing embodiments may further include a bias generator configured to receive the constant value corresponding to the actual phase angle and to output a biased phase angle to be used by the comparator as the actual phase angle.

Any of the foregoing embodiments may further include an angle reference module configured to compare deadtime data and matching inductor data and to output the desired phase.

In any of the foregoing embodiments, the controller is a proportional-integral-derivative (PID) controller configured to receive the phase difference and to output a controller signal to be used by the resonant inverter to reduce the phase difference.

In any of the foregoing embodiments, the resonant inverter includes a plurality of switches, and the controller signal corresponds to control of the plurality of switches of the resonant inverter.

In any of the foregoing embodiments, the power signal is configured for use by an excimer bulb.

In any of the foregoing embodiments, the system is configured for use on an aircraft.

Also disclosed is a system for controlling a power signal for zero voltage switching (ZVS). The system includes a resonant inverter having at least one switch and configured to output an inverter voltage and an inverter current. The system further includes a voltage zero crossing detection module configured to detect a zero voltage condition in response to the inverter voltage crossing zero volts. The system further includes a current zero crossing detection module configured to detect a zero current condition in response to the inverter current crossing zero amps. The system further includes a phase detect module configured to detect actual phase data corresponding to an actual phase angle between the inverter voltage and the inverter current based on the zero voltage condition and the zero current condition. The system further includes a comparator configured to determine a phase difference between a desired phase between the inverter voltage and the inverter current and the actual phase angle. The system further includes a controller configured to adjust a property of the at least one switch of the resonant inverter to reduce the phase difference based on the phase difference.

In any of the foregoing embodiments, the phase detect module includes: a voltage phase locked loop (PLL) module that receives voltage input corresponding to the zero voltage condition from the voltage zero crossing detection module; and a current PLL module that receives current input corresponding to the zero current condition from the current zero crossing detection module.

Any of the foregoing embodiments may further include an and module configured to receive an output of the voltage PLL module and an output of the current PLL module and to output an output signal in response to the output of the voltage PLL module and the output of the current PLL module both being true, wherein: the voltage PLL module further receives the output signal of the and module; the current PLL module further receives the output signal of the and module; and the actual phase data determined by the phase detect module is taken as the output of the voltage PLL module.

Any of the foregoing embodiments may further include: a low pass filter configured to receive the actual phase data from the phase detect module and to output a constant value corresponding to the actual phase angle; and a bias generator configured to receive the constant value corresponding to the actual phase angle and to output a biased phase angle to be used by the comparator as the actual phase angle.

Also disclosed is a method for controlling a power signal for zero voltage switching (ZVS). The method includes detecting, by a voltage zero crossing detection module, a zero voltage condition in response to an inverter voltage from a resonant inverter crossing zero volts. The method further includes detecting, by current zero crossing detection module, a zero current condition in response to an inverter current from the resonant inverter crossing zero amps. The method further includes detecting, by a phase detect module, actual phase data corresponding to an actual phase angle between the inverter voltage and the inverter current based on the zero voltage condition and the zero current condition. The method further includes determining, by a comparator, a phase difference between a desired phase between the inverter voltage and the inverter current and the actual phase angle. The method further includes adjusting, by a controller, a property of a resonant inverter to reduce the phase difference based on the phase difference.

Any of the foregoing embodiments may further include filtering, by a low pass filter, the actual phase data to output a constant value corresponding to the actual phase angle.

Any of the foregoing embodiments may further include outputting, by a bias generator, a based phase angle to be used by the comparator as the actual phase angle based on the constant value from the low pass filter.

Any of the foregoing embodiments may further include comparing, by an angle reference module, deadline data and matching inductor data to determine the desired phase.

In any of the foregoing embodiments, the property of the resonant inverter corresponds to at least one switch of the resonant inverter.

In any of the foregoing embodiments, the power signal is configured for use by an excimer bulb on an aircraft.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

The present disclosure is directed to a new system and method for controlling an excimer lamp in aviation applications. The concept relates to a resonant frequency tracking and adjusting approach for zero voltage switching (ZVS) under a parameter change of the excimer lamp. The system calculates a phase angle using a phase locked loop (PLL). A bias generator determines a leading and lagging status. The output may be used as a feedback signal for the ZVS and resonant frequency tracking control. In the proposed system, the angle present value (based on deadtime value and inductor value) may be calculated and used as a reference for ZVS and resonant frequency tracking. Technically, the reference is the phase angle and the range may be within negative 3 decibels. Based on the reference and feedback, the phase angle error is calculated. A proportional-integral-derivative (PID) controller may adjust a pulse-width modulation (PWM) count value.

Figure 1:
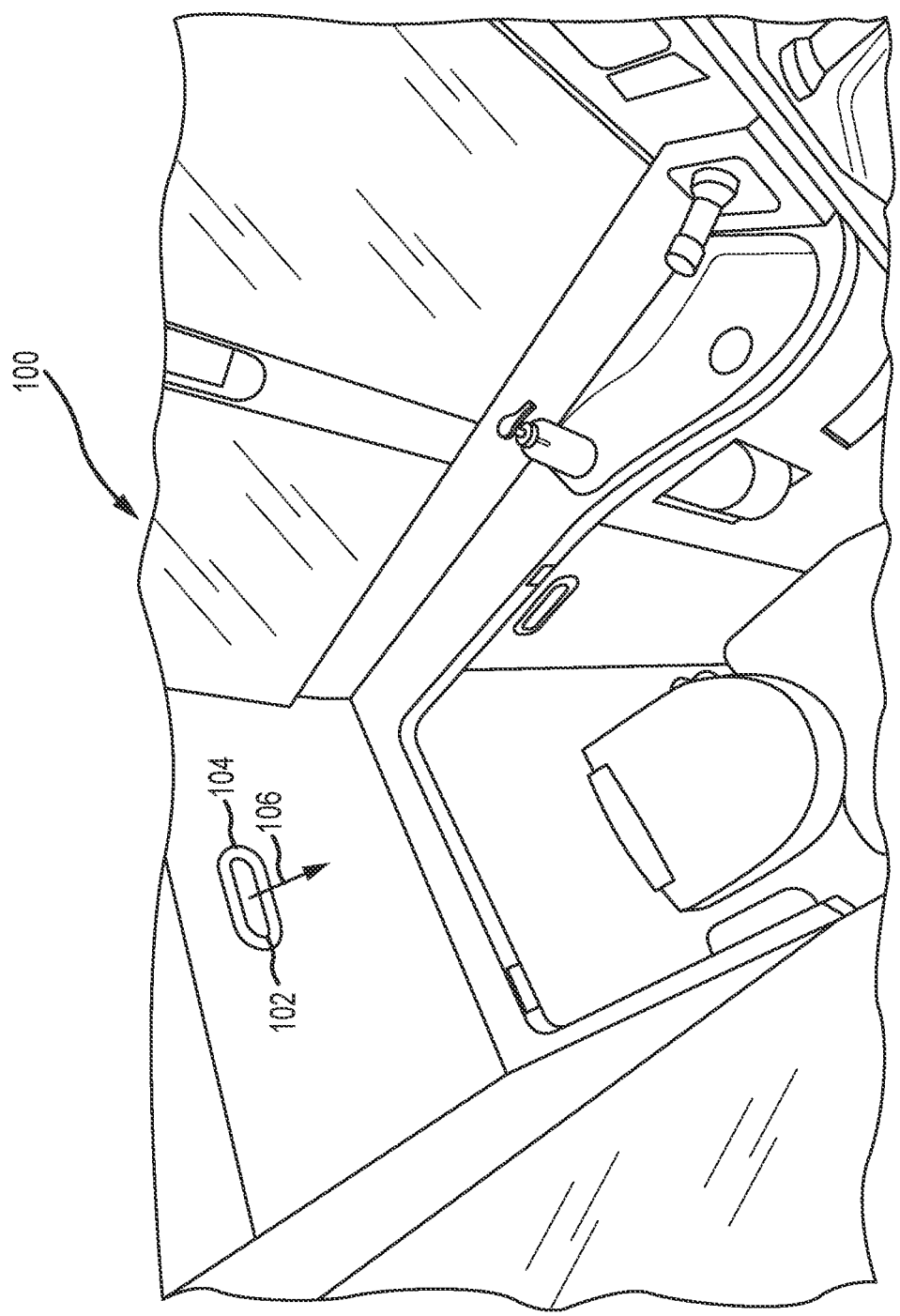
FIG. 1 illustrates an aircraft lavatory having an excimer ultraviolet bulb and a power supply for providing a power signal to the excimer bulb, in accordance with various embodiments.
Figure 2:
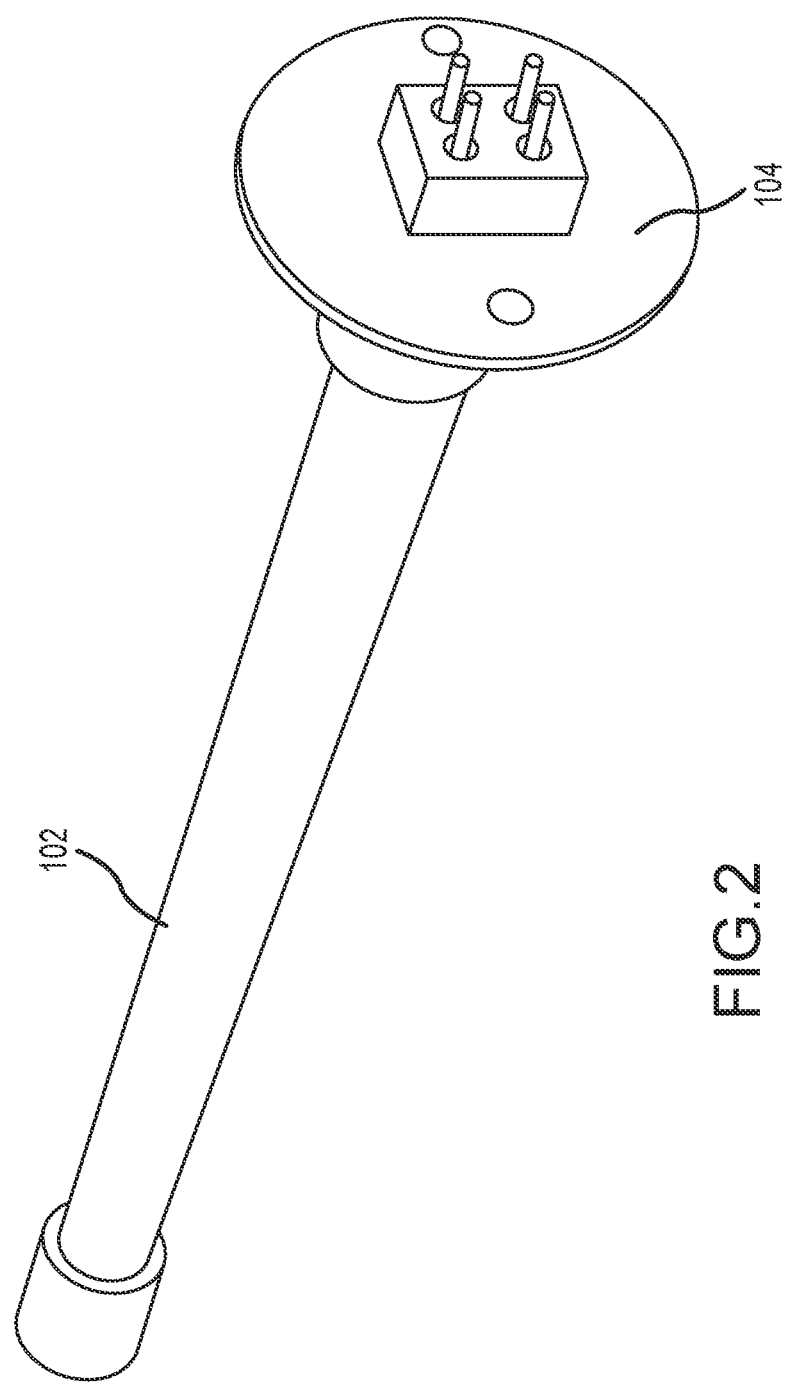
FIG. 2 is an enlarged view of the excimer bulb and the power supply of FIG. 1, in accordance with various embodiments.

Referring now to FIGS. 1 and 2, a portion of an aircraft lavatory 100 may include one or more UV excimer bulb 102. The excimer bulb 102 may emit UV light towards a portion of the lavatory 100, as shown by an arrow 106. The lavatory 100 may further include a power supply 104 designed to provide a power signal to the excimer bulb 102. In particular, the power supply 104 may provide a relatively high voltage power signal (i.e., between 500 volts and 3 kilovolts (3 kV), between 1 kV and 3 kV, or between 1.5 kV and 2.5 kV). The power supply 104 may be designed to receive either direct current (DC) input power or alternating current (AC) input power, and may output an AC output power signal. The power supply 104 may be designed to provide a desirable power signal to the excimer bulb 102 regardless of a status of the excimer bulb 102. That is, over time, the excimer bulb 102 may degrade and may have changing electrical properties as a result (e.g., a resistance or capacitance of the excimer bulb 102 may change over time). The power supply 104 is designed to compensate for these changing electrical properties of the excimer bulb 102.

Figure 3A:
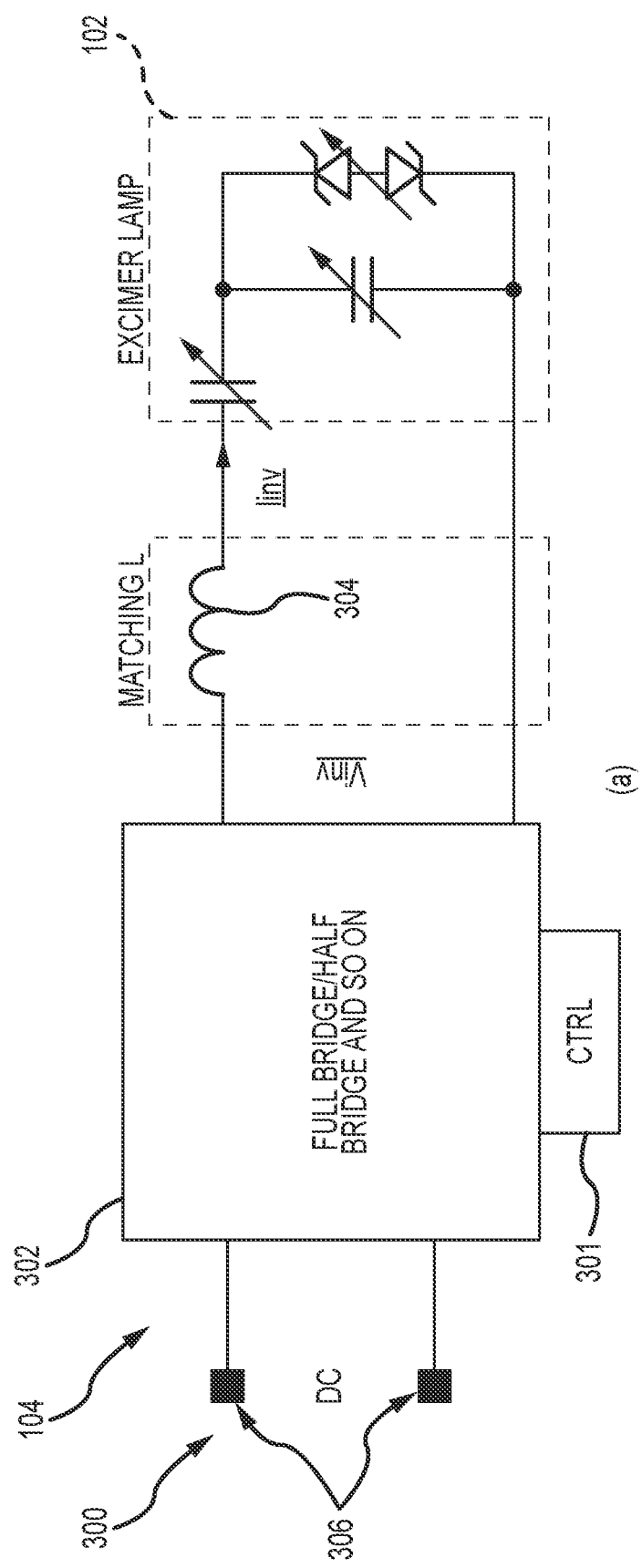
FIG. 3A is a schematic drawing illustrating a power circuit and a controller of the power supply of FIG. 1, in accordance with various embodiments.
Figure 3B:
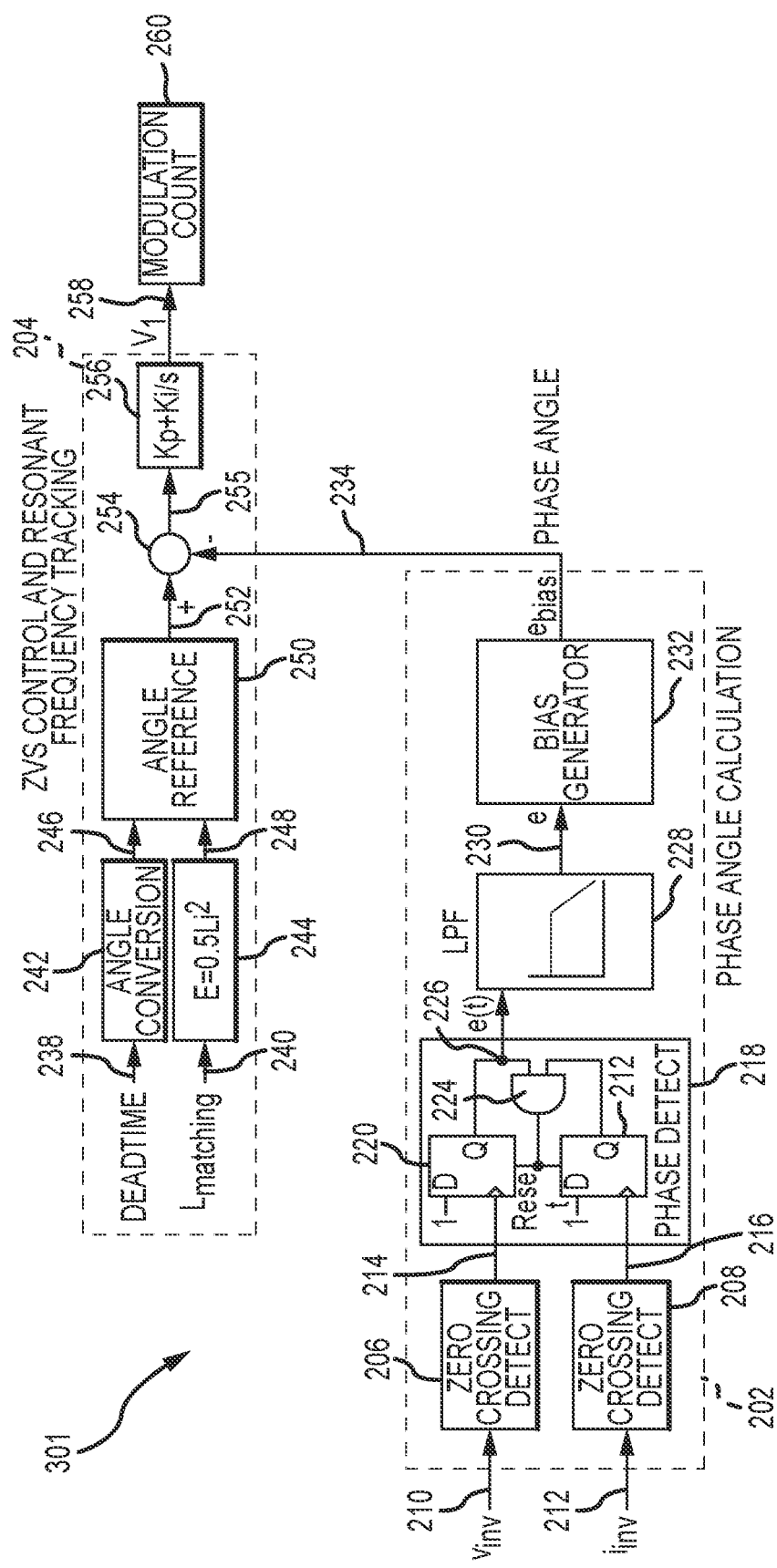
FIG. 3B is a schematic drawing illustrating various features of the controller of FIG. 3A, in accordance with various embodiments.

Referring now to FIGS. 3A and 3B, the power supply 104 may include a power circuit 300 and a controller 301. The power circuit 300 may include a bridge circuit 302 having one or more switch located therein, such as a transistor or any other switching circuit element. The bridge circuit 302 may receive an input voltage 306 and may generate a desirable waveform to control the excimer lamp 102 by controlling the switches. In that regard, the power circuit 300 may function as a resonant inverter.

The controller 301 may control operation of the switches in the bridge circuit 302 based on various parameters, as described in more detail below. The power circuit 300 may further include an inductor 304 which is used to match a resonant frequency of the excimer lamp 102. The output from the inductor 304 and the bridge circuit 302 may be used to power the excimer lamp 102. In various embodiments, the power circuit 300 may include any circuit with one or more switching element that can output power signals having a frequency usable to power the excimer lamp 102.

The controller 301 may include one or more logic devices such as one or more of a central processing unit (CPU), an accelerated processing unit (APU), a digital signal processor (DSP), a field programmable gate array (FPGA), an application specific integrated circuit (ASIC), or the like. In various embodiments, the controller 301 may further include any non-transitory memory known in the art. The memory may store instructions usable by the logic device to perform operations. The memory may also or instead store other data as instructed by the controller 301 such as calculated or desired phase angles.

The controller 301 may include various modules that perform specific functions. The functions of the modules may be implemented in hardware (e.g., transistors, logic gates, etc.), firmware, software, or any combination thereof.

In more detail and as shown in FIG. 3B, the controller 301 may include a phase angle calculation module 202 that calculates a phase angle between an input voltage (i.e., the voltage across the excimer lamp 102 in FIG. 3A) and an input current (i.e., the current flowing through the inductor 304). The controller 301 may further include a ZVS control and resonant frequency tracking module 204 outputs a signal usable to control the switch(es) of the power circuit 300.

The phase angle calculation module 202 may include a voltage zero crossing detection module 206 and a current zero crossing detection module 208. The voltage zero crossing detection module 206 may receive an inverter voltage signal 210 from a resonant inverter (e.g., the power circuit 300) and may detect a zero voltage condition corresponding to the inverter voltage signal 210 crossing zero volts. That is, the inverter voltage signal 210 may have a frequency and may alternate between positive and negative voltage values, and the voltage zero crossing detection module 206 may detect when the inverter voltage signal 210 reaches zero volts when switching from positive to negative or from negative to positive. The current zero crossing detection module 208 may receive an inverter current signal 212 from the resonant inverter and may detect a zero current condition corresponding to the inverter current signal 212 crossing zero volts. The voltage zero crossing detection module 206 may output a zero voltage signal 214 corresponding to the zero voltage condition detection. The current zero crossing detection module 208 may output a zero current signal 216 corresponding to the zero current condition.

A phase detect module 218 may receive the zero voltage signal 214 and the zero current signal 216 corresponding to the zero voltage condition and the zero current condition. The phase detect module 218 may detect or determine actual phase data 226 corresponding to an actual phase angle between the inverter voltage signal 210 and the inverter current signal 212 based on the zero voltage signal 214 and the zero current signal 216.

The phase detect module 218 may include a voltage phase locked loop (PLL) module 220 that receives the zero voltage signal 214, and a current PLL module 222 that receives the zero current signal 216. The phase detect module 218 may further include an and module 224 (which may function as an and gate) which receives the output of the voltage PLL module 220 and the output of the current PLL module 222. The and module 224 may output an output signal having a value of logical true in response to the output of both of the voltage PLL module 220 and the current PLL module 222 being a logical true. The output signal of the and module 224 may be fed into the voltage PLL module 220 and the current PLL module 222 as additional inputs. The output signal of the voltage PLL module 220 may be output as the actual phase data 226.

The actual phase data 226 may have noise in addition to a signal representing the actual phase angle between the inverter voltage signal 210 and the inverter current signal 212. In that regard, the actual phase data 226 from the phase detect module 218 may be received by a low pass filter (LPF) 228. The LPF 228 may filter the actual phase data 226 to remove noise having a relatively high frequency, and may output a constant value 230 that corresponds to the actual phase angle.

A bias generator 232 may receive the constant value 230 from the LPF 228 and may output a biased phase angle 234 corresponding to the actual phase angle between the inverter voltage signal 210 and the inverter current signal 212. In particular, the bias generator 232 may add a bias voltage to the constant value 230 such that the biased phase angle 234 may operate in a preferred voltage region.

The ZVS control and resonant frequency tracking module 204 may receive or determine a deadtime signal 238 and a matching inductance signal 240. The deadtime signal 238 may correspond to a period of time in which all switches of the control circuit 300 are switched off and it allows for reduction or elimination of a short circuit effect within the control circuit 300. The matching inductance signal 240 corresponds to the inductance of the inductor 304.

The deadtime signal 238 may be received by an angle conversion module 242 which converts the deadtime signal 238 into an angle signal 246. The matching inductance signal 240 may be received by an energy calculation module 244 which may calculate an energy signal 248 corresponding to an amount of energy at the inductor 304 based on the inverter current 212 and the matching inductance signal 240.

An angle reference module 250 may receive the angle signal 246 and the energy signal 248 and may calculate or determine a desired phase angle 252 between the inverter voltage signal 210 and the inverter current signal 212 based on the angle signal 246 and the energy signal 248. The desired phase angle 252 may be an angle at which the output of the resonant inverter may be used to properly power the excimer lamp 102 and may be based on the changing electrical properties of the excimer lamp 102. As referenced above, the electrical properties of the excimer lamp 102 may vary as the excimer lamp 102 is used.

A comparator 254 may receive the desired phase angle 252 and the biased phase angle 234 and may determine a difference signal 255 corresponding to a difference in value between the desired phase angle 252 and the biased phase angle 234. A PID controller 256 may receive the difference signal 255 and may output a controller signal 258 based on the difference signal 255. The controller signal 258 may be used to control the switches of the resonant inverter. The PID controller 256 may continue to adjust the controller signal 258 to reduce the phase difference between the desired phase angle 252 and the biased phase angle 234 (i.e., the actual phase angle). A modulus 260 may be the specific signals used by the controller 301 to control the switches of the resonant inverter and may be based on the controller signal 258.

The controller 301 may provide several benefits and advantages over conventional controllers that are used to control excimer lamps. In particular, the controller 301 achieves true zero voltage switching, which reduces power loss which may occur when ZVS fails to function properly (as is the case in conventional controllers when an excimer lamp degrades such that its electrical properties change). Additionally, the controller 301 achieves reduced electromagnetic interference (EMI) relative to conventional controllers by avoiding turn on transient values. Also, the controller 301 continues to provide a desired output voltage signal to the excimer lamp regardless of the changing electrical properties of the excimer lamp, which conventional controllers fail to provide.

Figure 4:
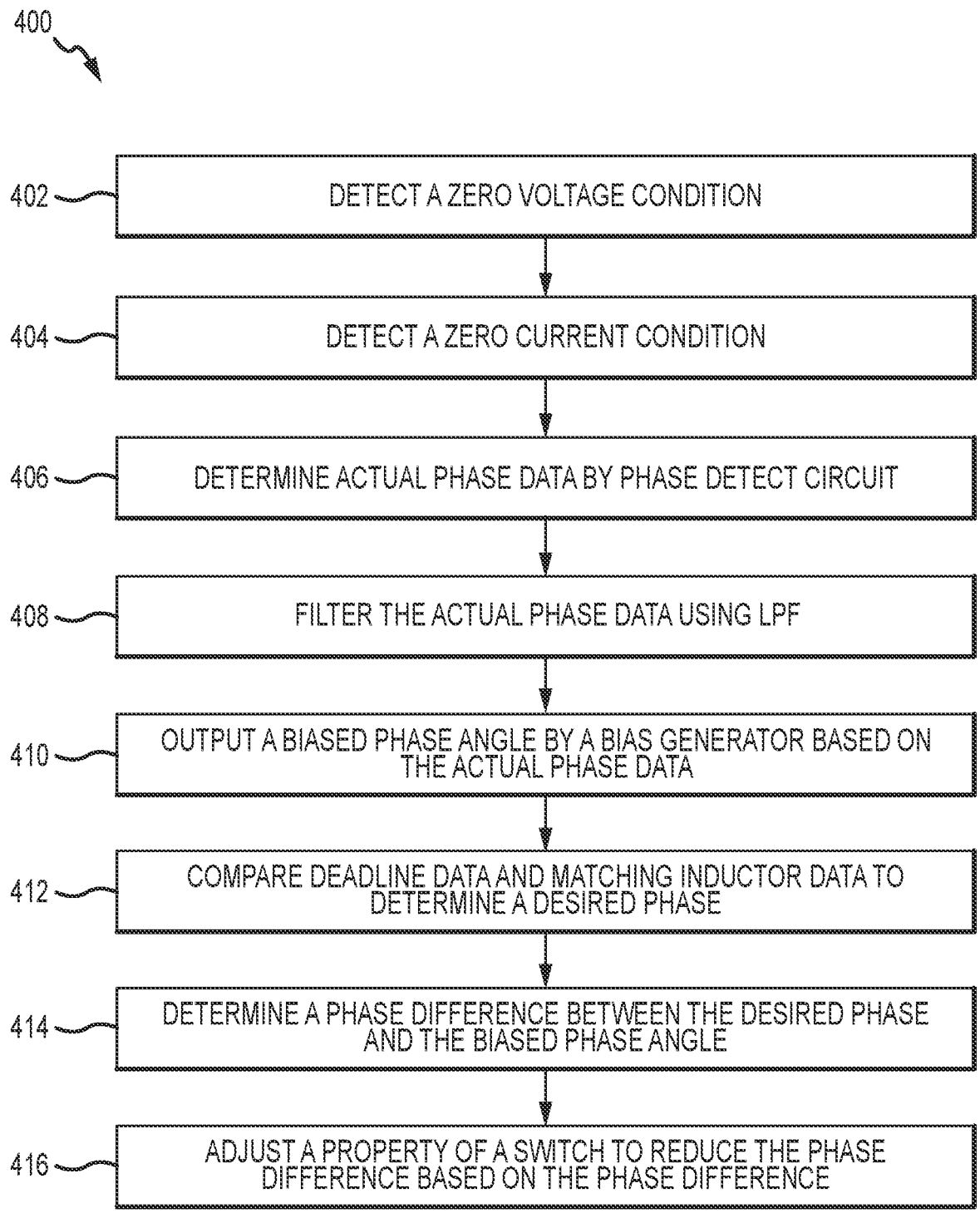
FIG. 4 is a flowchart illustrating a method for controlling a power signal for zero voltage switching, in accordance with various embodiments.

Referring now to FIG. 4, a method 400 for controlling a power signal for ZVS control of an excimer bulb is shown. The method 400 may be implemented using similar features as the controller 301 of FIGS. 3A and 3B.

The method 400 may begin in block 402 by detecting a zero voltage condition of an inverter voltage signal used to power an excimer bulb. In block 404, a zero current condition of an inverter current signal may be detected.

In block 406, a phase detect circuit may detect actual phase data corresponding to a phase angle between the inverter voltage signal and the inverter current signal. In block 408, a LPF may be used to filter the actual phase data, which may result in a constant phase angle signal. In block 410, a bias generator may output a biased phase angle based on the constant phase angle from the LPF.

In block 412, deadline data and matching inductor data may be compared to determine a desired phase angle between the inverter voltage signal and the inverter current signal. In block 414, a comparator may determine a phase difference between the desired phase angle and the biased (i.e., actual) phase angle. In block 416, a PID controller may adjust a property of at least one switch in of a resonant inverter to reduce the phase difference. The PID controller may adjust the property based on the phase difference that is output by the comparator.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 12(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for controlling a power signal for zero voltage switching (ZVS), the system comprising:
   a voltage zero crossing detection module configured to detect a zero voltage condition in response to an inverter voltage from a resonant inverter crossing zero volts;
   a current zero crossing detection module configured to detect a zero current condition in response to an inverter current from the resonant inverter crossing zero amps;
   a phase detect module configured to detect actual phase data corresponding to an actual phase angle between the inverter voltage and the inverter current based on the zero voltage condition and the zero current condition;
   a comparator configured to determine a phase difference between a desired phase between the inverter voltage and the inverter current and the actual phase angle; and
   a controller configured to adjust a property of a resonant inverter to reduce the phase difference based on the phase difference.

2. The system of claim 1, wherein the phase detect module includes:
a voltage phase locked loop (PLL) module that receives voltage input corresponding to the zero voltage condition from the voltage zero crossing detection module; and
a current PLL module that receives current input corresponding to the zero current condition from the current zero crossing detection module.

3. The system of claim 2, further comprising an and module configured to receive an output of the voltage PLL module and an output of the current PLL module and to output an output signal in response to the output of the voltage PLL module and the output of the current PLL module both being true, wherein:
the voltage PLL module further receives the output signal of the and module;
the current PLL module further receives the output signal of the and module; and
the actual phase data determined by the phase detect module is taken as the output of the voltage PLL module.

4. The system of claim 3, further comprising a low pass filter configured to receive the actual phase data from the phase detect module and to output a constant value corresponding to the actual phase angle.

5. The system of claim 4, further comprising a bias generator configured to receive the constant value corresponding to the actual phase angle and to output a biased phase angle to be used by the comparator as the actual phase angle.

6. The system of claim 1, further comprising an angle reference module configured to compare deadtime data and matching inductor data and to output the desired phase.

7. The system of claim 1, wherein the controller is a proportional-integral-derivative (PID) controller configured to receive the phase difference and to output a controller signal to be used by the resonant inverter to reduce the phase difference.

8. The system of claim 7, wherein the resonant inverter includes a plurality of switches, and the controller signal corresponds to control of the plurality of switches of the resonant inverter.

9. The system of claim 1, wherein the power signal is configured for use by an excimer bulb.

10. The system of claim 9, wherein the system is configured for use on an aircraft.

11. A system for controlling a power signal for zero voltage switching (ZVS), the system comprising:
a resonant inverter having at least one switch and configured to output an inverter voltage and an inverter current;
a voltage zero crossing detection module configured to detect a zero voltage condition in response to the inverter voltage crossing zero volts;
a current zero crossing detection module configured to detect a zero current condition in response to the inverter current crossing zero amps;
a phase detect module configured to detect actual phase data corresponding to an actual phase angle between the inverter voltage and the inverter current based on the zero voltage condition and the zero current condition;
a comparator configured to determine a phase difference between a desired phase between the inverter voltage and the inverter current and the actual phase angle; and
a controller configured to adjust a property of the at least one switch of the resonant inverter to reduce the phase difference based on the phase difference.

12. The system of claim 11, wherein the phase detect module includes:
a voltage phase locked loop (PLL) module that receives voltage input corresponding to the zero voltage condition from the voltage zero crossing detection module; and
a current PLL module that receives current input corresponding to the zero current condition from the current zero crossing detection module.

13. The system of claim 12, further comprising an and module configured to receive an output of the voltage PLL module and an output of the current PLL module and to output an output signal in response to the output of the voltage PLL module and the output of the current PLL module both being true, wherein:
the voltage PLL module further receives the output signal of the and module;
the current PLL module further receives the output signal of the and module; and
the actual phase data determined by the phase detect module is taken as the output of the voltage PLL module.

14. The system of claim 13, further comprising:
a low pass filter configured to receive the actual phase data from the phase detect module and to output a constant value corresponding to the actual phase angle; and
a bias generator configured to receive the constant value corresponding to the actual phase angle and to output a biased phase angle to be used by the comparator as the actual phase angle.

15. A method for controlling a power signal for zero voltage switching (ZVS), the method comprising:
detecting, by a voltage zero crossing detection module, a zero voltage condition in response to an inverter voltage from a resonant inverter crossing zero volts;
detecting, by current zero crossing detection module, a zero current condition in response to an inverter current from the resonant inverter crossing zero amps;
detecting, by a phase detect module, actual phase data corresponding to an actual phase angle between the inverter voltage and the inverter current based on the zero voltage condition and the zero current condition;
determining, by a comparator, a phase difference between a desired phase between the inverter voltage and the inverter current and the actual phase angle; and
adjusting, by a controller, a property of a resonant inverter to reduce the phase difference based on the phase difference.

16. The method of claim 15, further comprising filtering, by a low pass filter, the actual phase data to output a constant value corresponding to the actual phase angle.

17. The method of claim 16, further comprising outputting, by a bias generator, a based phase angle to be used by the comparator as the actual phase angle based on the constant value from the low pass filter.

18. The method of claim 15, further comprising comparing, by an angle reference module, deadline data and matching inductor data to determine the desired phase.

19. The method of claim 15, wherein the property of the resonant inverter corresponds to at least one switch of the resonant inverter.

20. The method of claim 15, wherein the power signal is configured for use by an excimer bulb on an aircraft.

\* \* \* \* \*